United States Patent
Srinivasan

(10) Patent No.: US 12,020,698 B2
(45) Date of Patent: Jun. 25, 2024

(54) ELECTRONIC HEALTH RECORD NAVIGATION

(71) Applicant: MedicalMine, Inc., Pleasanton, CA (US)

(72) Inventor: Pramila Srinivasan, Pleasanton, CA (US)

(73) Assignee: MedicalMine, Inc., Pleasanton, CA (US)

(*) Notice: Subject to any disclaimer, the term of this patent is extended or adjusted under 35 U.S.C. 154(b) by 168 days.

(21) Appl. No.: 17/092,156

(22) Filed: Nov. 6, 2020

(65) Prior Publication Data

US 2021/0174800 A1 Jun. 10, 2021

Related U.S. Application Data

(63) Continuation-in-part of application No. 14/838,309, filed on Aug. 27, 2015.

(60) Provisional application No. 62/042,461, filed on Aug. 27, 2014.

(51) Int. Cl.

| | |
|---|---|
| *G10L 15/22* | (2006.01) |
| *G06F 3/04817* | (2022.01) |
| *G06F 3/16* | (2006.01) |
| *G06F 40/205* | (2020.01) |
| *G10L 15/18* | (2013.01) |
| *G10L 15/30* | (2013.01) |
| *G16H 10/60* | (2018.01) |

(52) U.S. Cl.
CPC .......... *G10L 15/22* (2013.01); *G06F 3/04817* (2013.01); *G06F 3/167* (2013.01); *G06F 40/205* (2020.01); *G10L 15/1822* (2013.01); *G10L 15/30* (2013.01); *G16H 10/60* (2018.01); *G10L 2015/223* (2013.01); *G10L 2015/227* (2013.01); *G10L 2015/228* (2013.01)

(58) Field of Classification Search
CPC ..... G10L 15/22; G10L 15/1822; G10L 15/30; G10L 2015/223; G10L 2015/227; G10L 2015/228; G06F 3/04817; G06F 3/167; G06F 40/205; G06F 3/04895; G16H 10/60; G16H 40/67
See application file for complete search history.

(56) References Cited

U.S. PATENT DOCUMENTS

| | | | |
|---|---|---|---|
| 11,398,232 B1* | 7/2022 | Agassi | G06F 40/30 |
| 11,410,650 B1* | 8/2022 | Agassi | G10L 15/1822 |
| 2004/0122736 A1 | 6/2004 | Strock et al. | |
| 2011/0184748 A1 | 7/2011 | Fierro et al. | |
| 2012/0129139 A1 | 5/2012 | Partovi | |
| 2014/0278139 A1 | 9/2014 | Hong et al. | |
| 2016/0232329 A1* | 8/2016 | Xu | G06F 40/186 |
| 2021/0397788 A1* | 12/2021 | Yim | G06F 3/04817 |

* cited by examiner

*Primary Examiner* — Gregory D. Moseley
(74) *Attorney, Agent, or Firm* — Ahmann Kloke LLP

(57) ABSTRACT

A technique involves providing a natural language interface to an electronic health record (EHR) system to enable a user to navigate the system efficiently. One or more input stimuli are received from the user via the natural language interface and converted into one or more commands that are used to change a navigational or other state of the EHR system. In an embodiment, the one or more commands are displayed in a navigation prioritized list. In an embodiment, the natural language interface is incorporated into an Internet of Things (IoT) device.

20 Claims, 12 Drawing Sheets

```
Q ▼   list
```

... allergy for <patient>                               450-1
... injections for <patient>                            450-2
... vaccine for <patient>
... charts to be billed for <patient>
... encounter for <patient>
... appointment for <patient>
... lab order for <patient>
... lab result for <patient>                            ...
... document for <patient>
... invoice for <patient>
... messages for <patient>
... tasks for <patient>
... diagnosis for <patient>
... vitals for <patient>
... recall for <patient>
... quick notes for <patient>
... sticky for <patient>                                450-n

FIG. 4

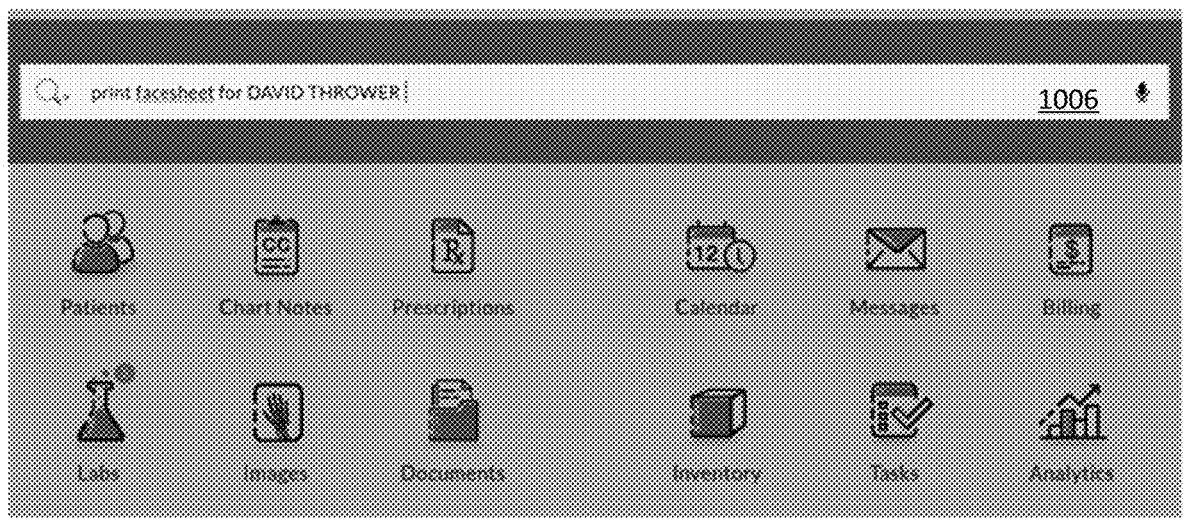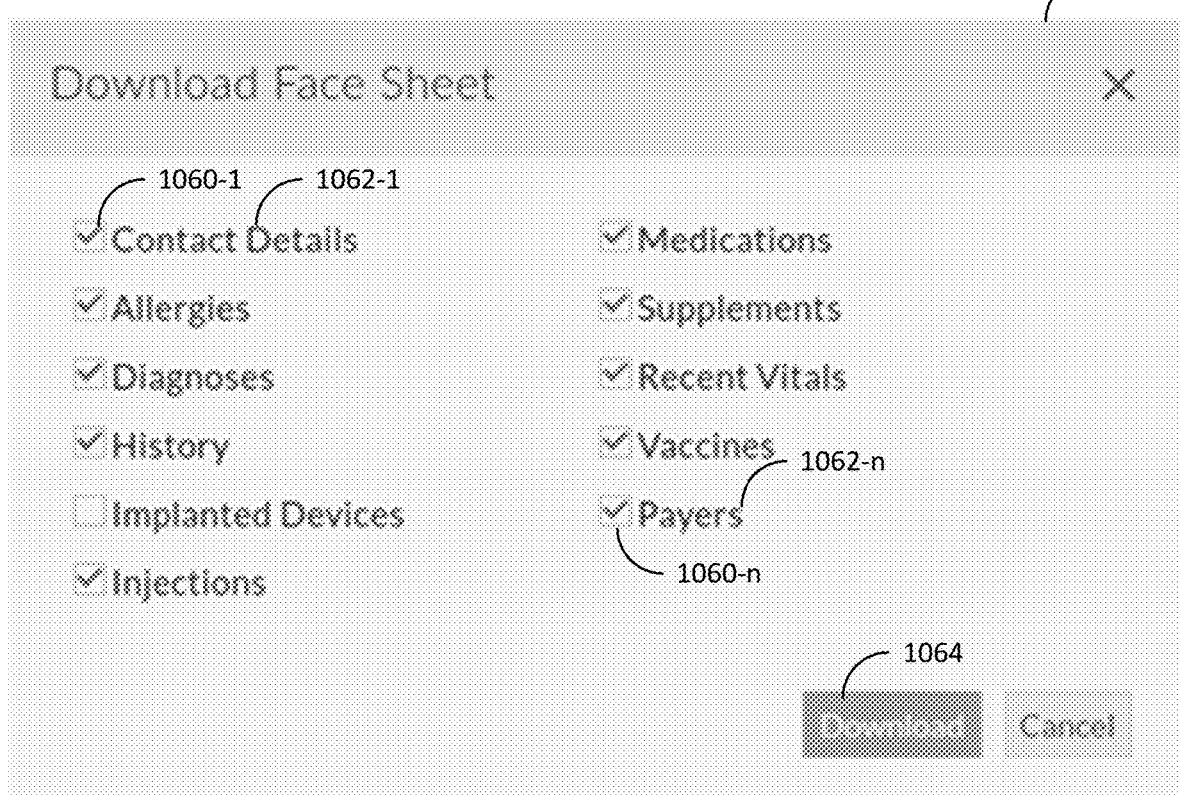
FIG. 10

ELECTRONIC HEALTH RECORD NAVIGATION

CROSS-REFERENCE TO RELATED APPLICATIONS

The present application is a continuation-in-part of U.S. patent application Ser. No. 14/838,309 filed Aug. 27, 2015 and entitled "Patient Health Record Portal Gamification," which claims priority to U.S. Provisional patent Application Ser. No. 62/042,461 filed Aug. 27, 2014 and entitled "Patient Health Record Portal Gamification," which are hereby incorporated by reference herein.

BACKGROUND

The availability and growth of telehealth is expanding specialist access, sometimes even to extremely remote locations. The ability to retrieve and share health information across Health Information Exchanges is making up-to-date healthcare information available across countries and even internationally. Physicians can order labs and prescriptions online and patients are able to have access to online orders and progress tracking. In this context, the efficiencies and conveniences afforded by Electronic Health Records (EHRs) and connected networks of secure Personal Health Information (PHI) are undeniable.

In an EHR system used in an ambulatory or hospital setting, professionals interact with the system from different terminals, usually even for the same patient encounter with a physician. In most cases, physicians are required to carry out a series of workflow steps, including taking patient demographics, history, and updating current medications. Following this, a physician typically takes the chart note in a Subjective, Objective, Assessment and Plan (SOAP) format. This includes identifying symptoms, making notes, prescribing drugs, sending electronic prescriptions to a pharmacy, and sending lab orders to a lab. At the end of this process, the physician generates an invoice or submits the bill to insurance, or a combination of both. In most cases, the physician has staff to perform one or more of these functions.

An impediment to EHR use is data entry complexity and data access limitations, particularly when a medical provider is simultaneously interacting with a patient and making medical decisions. A typical EHR system is complex, with many features, options, and layers of navigation menus. In a typical medical office, time is scarce, but accuracy is essential.

An invention that positively impacts usability of EHRs could provide benefits such as increased adoption of EHRs by stakeholders, improved provider satisfaction, and improved patient care, to name a few.

SUMMARY

A technique involves providing a natural language interface to an electronics health record (EHR) system to enable a user to navigate the system efficiently. There are multiple benefits to usability, speed of access to medical records, leading to faster and more efficient care, and user satisfaction. An applicable system incorporates a command language that enables a medical professional to use domain-specific language and terminology to navigate the EHR system using few or no clicks. Using a language syntax, natural language commands can get a human to a desired screen to perform a desired function using almost no clicks. The language can be entered using voice input or keyboard. One or more language enhancements are possible—including using the context of a user, a history of past commands, a current workflow, and relevant information about a patient—to give a prioritized list of past commands as autosuggestions to a command interface.

Machine learning is used to predict human interaction, workflow, and context, and to improve upon commands given through a natural language interface, by voice or text. Input devices range from desktop to mobile devices, Internet-enabled wireless devices and systems, and mobile clients connected through a web browser, on-site, or remote and ambulatory platforms. This system will enable rapid and efficient access to information and entry into the EHR system for medical professionals and other users of the system, resulting in an enhanced user and patient experience.

BRIEF DESCRIPTION OF THE DRAWINGS

FIG. 4 depicts a screenshot of an example of an EHR natural language navigation dashboard displaying a command string.

FIG. 10 is a screenshot of an example of an EHR natural language navigation dashboard displaying the command string "print facesheet for David Thrower" in a navigation text box.

DETAILED DESCRIPTION

Figure 1:
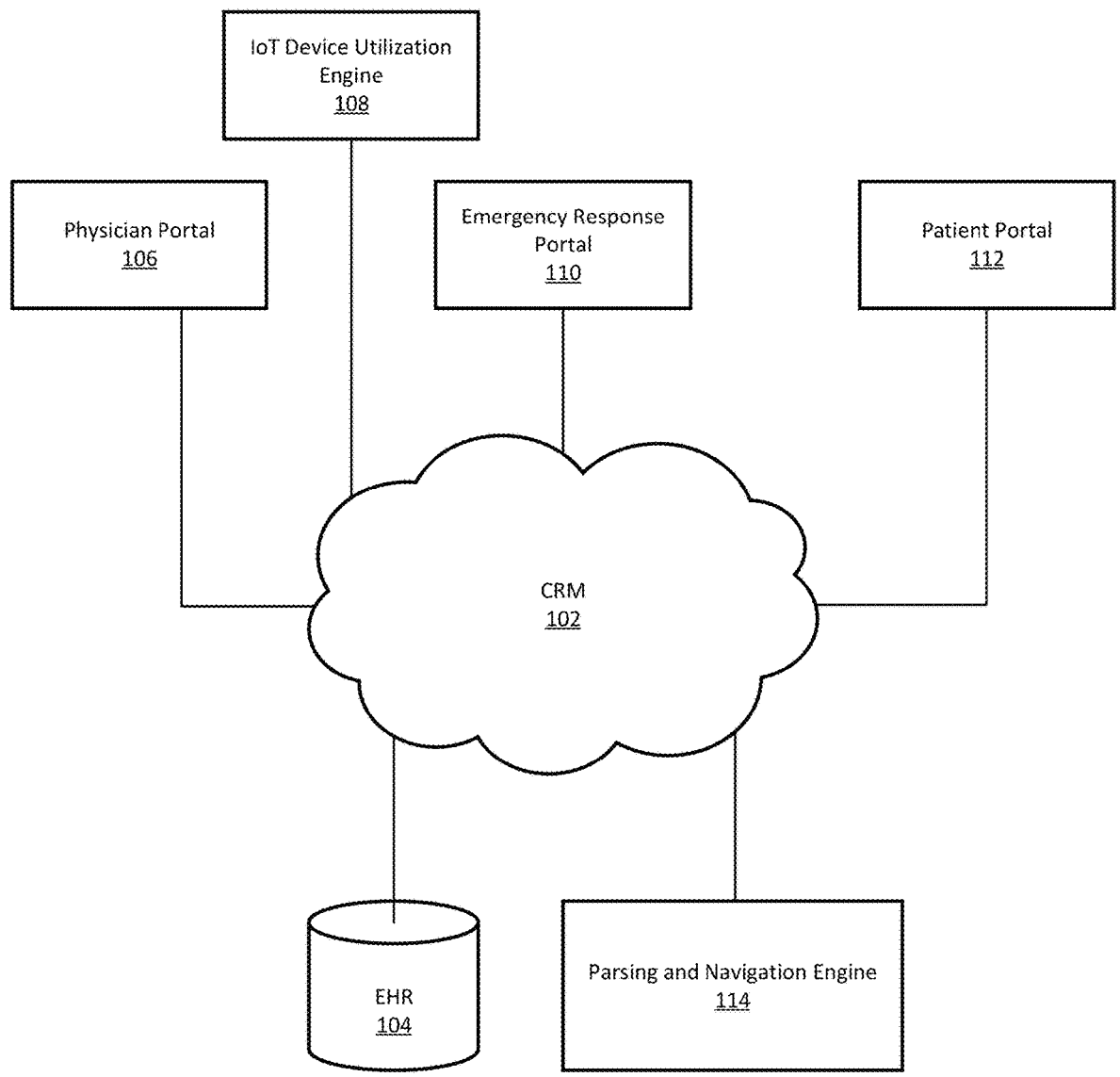
FIG. 1 depicts a diagram of an example of an EHR natural language navigation system.

FIG. 1 depicts a diagram 100 of an example of an electronic health record (EHR) natural language navigation system. The system can provide a simple familiar interface to an EHR, Practice Management (PM) and Revenue Cycle Management (RCM) cloud-based ecosystem. The diagram 100 includes a computer-readable medium (CRM) 102, an EHR datastore 104 coupled to the CRM 102, a physician portal 106 coupled to the CRM 102, an Internet of Things (IoT) device utilization engine 108 coupled to the CRM 102, an emergency response portal 110 coupled to the CRM 102, a patient portal 112 coupled to the CRM 102, and a parsing and navigation engine 114 coupled to the CRM 102.

The CRM 102 may comprise a computer system or network of computer systems. A "computer system," as used herein, may include or be implemented as a specific purpose computer system for carrying out the functionalities described in this paper. In general, a computer system will include a processor, memory, non-volatile storage, and an interface. A typical computer system will usually include at least a processor, memory, and a device (e.g., a bus) coupling the memory to the processor. The processor can be, for example, a general-purpose central processing unit (CPU), such as a microprocessor, or a special-purpose processor, such as a microcontroller.

Memory of a computer system includes, by way of example but not limitation, random access memory (RAM), such as dynamic RAM (DRAM) and static RAM (SRAM). The memory can be local, remote, or distributed. Non-volatile storage is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. During execution of software, some of this data is often written, by a direct memory access process, into memory by way of a bus coupled to non-volatile storage. Non-volatile storage can be local, remote, or distributed, but is optional because systems can be created with all applicable data available in memory.

Software in a computer system is typically stored in non-volatile storage. Indeed, for large programs, it may not even be possible to store the entire program in memory. For software to run, if necessary, it is moved to a computer-readable location appropriate for processing, and for illustrative purposes in this paper, that location is referred to as memory. Even when software is moved to memory for execution, a processor will typically make use of hardware registers to store values associated with the software, and a local cache that, ideally, serves to speed up execution. As used herein, a software program is assumed to be stored at an applicable known or convenient location (from non-volatile storage to hardware registers) when the software program is referred to as "implemented in a computer-readable storage medium." A processor is considered "configured to execute a program" when at least one value associated with the program is stored in a register readable by the processor.

In one example of operation, a computer system can be controlled by operating system software, which is a software program that includes a file management system, such as a disk operating system. One example of operating system software with associated file management system software is the family of operating systems known as Windows from Microsoft Corporation of Redmond, Wash., and their associated file management systems. Another example of operating system software with its associated file management system software is the Linux operating system and its associated file management system. The file management system is typically stored in the non-volatile storage and causes the processor to execute the various acts required by the operating system to input and output data and to store data in the memory, including storing files on the non-volatile storage.

The bus of a computer system can couple a processor to an interface. Interfaces facilitate the coupling of devices and computer systems. Interfaces can be for input and/or output (I/O) devices, modems, or networks. I/O devices can include, by way of example but not limitation, a keyboard, a mouse or other pointing device, disk drives, printers, a scanner, and other I/O devices, including a display device. Display devices can include, by way of example but not limitation, a cathode ray tube (CRT), liquid crystal display (LCD), or some other applicable known or convenient display device. Modems can include, by way of example but not limitation, an analog modem, an IDSN modem, a cable modem, and other modems. Network interfaces can include, by way of example but not limitation, a token ring interface, a satellite transmission interface (e.g. "direct PC"), or other network interface for coupling a first computer system to a second computer system. An interface can be considered part of a device or computer system.

Computer systems can be compatible with or implemented as part of or through a cloud-based computing system. As used in this paper, a cloud-based computing system is a system that provides virtualized computing resources, software and/or information to client devices. The computing resources, software and/or information can be virtualized by maintaining centralized services and resources that the edge devices can access over a communication interface, such as a network. "Cloud" may be a marketing term and for the purposes of this paper can include any of the networks described herein. The cloud-based computing system can involve a subscription for services or use a utility pricing model. Users can access the protocols of the cloud-based computing system through a web browser or other container application located on their client device.

A computer system can be implemented as an engine, as part of an engine, or through multiple engines. As used in this paper, an engine includes at least two components: 1) a dedicated or shared processor or a portion thereof; 2) hardware, firmware, and/or software modules executed by the processor. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors, or a first engine and a second engine can share one or more processors with one another or other engines. Depending upon implementation-specific or other considerations, an engine can be centralized, or its functionality distributed. An engine can include hardware, firmware, or software embodied in a computer-readable medium for execution by the processor. The processor transforms data into new data using implemented data structures and methods, such as is described with reference to the figures in this paper.

The engines described in this paper, or the engines through which the systems and devices described in this paper can be implemented, can be cloud-based engines. As used in this paper, a cloud-based engine is an engine that can run applications and/or functionalities using a cloud-based computing system. All or portions of the applications and/or functionalities can be distributed across multiple computing devices and need not be restricted to only one computing device. In some embodiments, the cloud-based engines can execute functionalities and/or modules that end users access through a web browser or container application without having the functionalities and/or modules installed locally on the end-users' computing devices.

As used in this paper, datastores are intended to include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a general- or specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described in this paper.

Datastores can include data structures. As used in this paper, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described in this paper, can be cloud-based datastores. A cloud based datastore is a datastore that is compatible with cloud-based computing systems and engines.

Assuming a CRM includes a network, the network can be an applicable communications network, such as the Internet or an infrastructure network. The term "Internet" as used in this paper refers to a network of networks that use certain protocols, such as the TCP/IP protocol, and possibly other protocols, such as the hypertext transfer protocol (HTTP) for hypertext markup language (HTML) documents that make up the World Wide Web ("the web"). More generally, a network can include, for example, a wide area network (WAN), metropolitan area network (MAN), campus area network (CAN), or local area network (LAN), but the network could at least theoretically be of an applicable size or characterized in some other fashion (e.g., personal area network (PAN) or home area network (HAN), to name a couple of alternatives). Networks can include enterprise private networks and virtual private networks (collectively, private networks). As the name suggests, private networks are under the control of a single entity. Private networks can include a head office and optional regional offices (collectively, offices). Many offices enable remote users to connect to the private network offices via some other network, such as the Internet.

Referring once again to the example of FIG. 1, the EHR datastore 104 is intended to represent a datastore of EHRs.

The physician portal 106 is intended to represent an engine that enables a physician or human or artificial agent thereof to access the electronic health record datastore 104. In a specific implementation, the physician portal 106 includes a cloud-based service accessible via a computer in, e.g., a hospital. Advantageously, in a specific implementation, context-based navigation is supported.

The IoT device utilization engine 108 is intended to represent an engine that monitors IoT devices, in particular medical IoT devices, and establishes context in association with IoT devices. In a specific implementation, the IoT device utilization engine 108 facilitates EHR datastore 104 CRUD access by Internet-enabled devices. For example, the IoT device utilization engine 108 could, responsive to a voice command such as "Record blood pressure for patient John Smith," push historical or state information from an internet-enabled blood pressure monitor to the EHR datastore 104. While useful in hospitals and medical offices, in a specific implementation, the IoT device utilization engine 108 is implemented in association with mobile vehicular installations and would likely be desirable in scenarios in which medical professionals need rapid access to patient records while diagnosing and/or treating the patient.

The emergency response portal 110 is intended to represent an engine that enables a paramedic or other emergency response professional, an agent thereof, or someone acting in such a capacity even if not a professional, to access the EHR datastore 104. Even on relatively simple interfaces with a touch or voice-based input, a mobile system could be used as an interface to the EHR datastore 104. In a situation where rapid navigation to a patient's health records are needed, a command language interface and voice commands could be used to issue commands to retrieve information that might be vital in an emergency. Examples of such commands could include: List medication allergies for John Smith, List current prescription medications for John Smith, List current diagnoses for John Smith, etc.

The patient portal 112 is intended to represent an engine that provides access to the EHR datastore 104 for a patient or agent thereof. In a specific implementation, the patient portal is implemented as a component of a modern EHR system for accessing Patient Health Records (PHR) to facilitate seamless communications and/or encourage patient engagement. A typical PHR provides tools for scheduling, messaging to the physician office, prescription refill requests and similar tools. A version of the command language can be used to handle patient side user interface. For example: List current medications, Request refill for Prednisone, etc.

Advantageously, patients can be recruited from remote sites and their regular check-in and monitoring happens through an internet enabled device, mobile phone, browser or custom application. The ability to reduce costs on clinical research management systems is critical, and the ability to carry on clinical trials using telehealth and other remote monitoring features with efficient navigation capabilities helps bring down costs and accelerates research for the benefit of rapid new research and drug discovery. Clinical researchers can enter commands at the physician portal 106 such as List patients with a diagnosis of Major Depression, List recent Bristol Stool Scale info for John Smith, List Bristol Scale for John Smith, etc.

The parsing and navigation engine 114 is intended to represent an engine that obtains input stimuli (usually text, voice, or activation of icons) via an applicable input device and converts the input stimuli to commands used to change navigational or other state.

Figure 2:
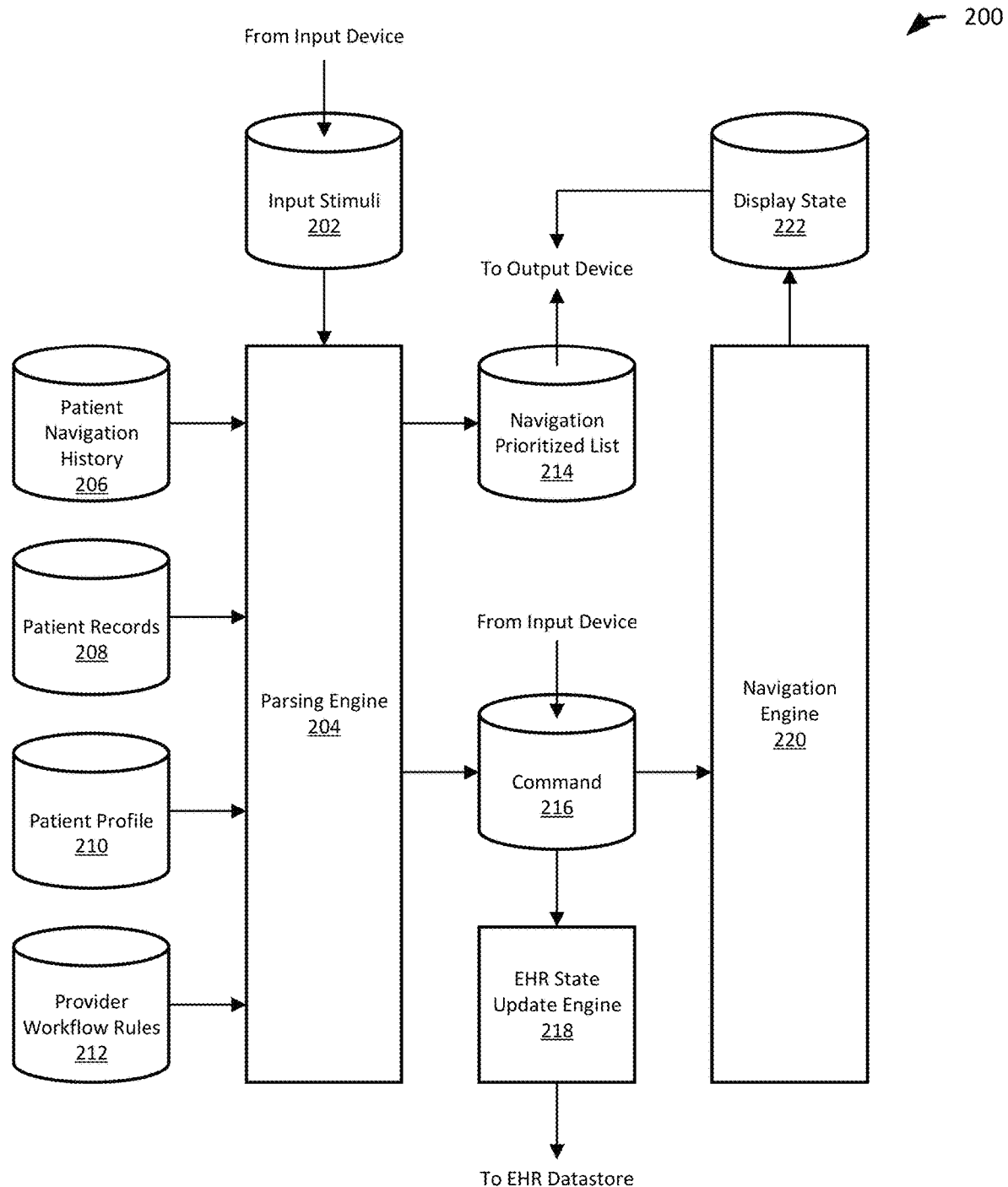
FIG. 2 is a diagram of an EHR system parsing and navigation engine.

FIG. 2 is a diagram 200 of an EHR system parsing and navigation engine. The diagram 200 includes an input stimuli datastore 202, a parsing engine 204 coupled to the input stimuli datastore 202, a patient navigation history datastore 206 coupled to the parsing engine 204, a patient records datastore 208 coupled to the parsing engine 204, a patient profile datastore 210 coupled to the parsing engine 204, a provider workflow rules datastore 212 coupled to the parsing engine 204, a navigation prioritized list datastore 214 coupled to the parsing engine 204, a command datastore 216 coupled to the parsing engine 204, an EHR state update engine 218 coupled to the command datastore 216, a navigation engine 220 coupled to the command datastore 216, and a display state datastore 222 coupled to the navigation engine 220.

The input stimuli datastore 202 is intended to represent a datastore of text, sound, or other data collected by an input device (not shown). The input stimuli datastore 202 can include data that is not useful for parsing an intended command, such as noise, redundancy, verbosity, or the like.

The parsing engine 204 is intended to represent an engine that extracts an intended command syntax from data in the input stimuli datastore 202. In a specific implementation, the parsing engine 204 includes enough variation of syntax of a language to allow the re-arrangement of linguistic components from the input stimuli datastore 202 into a command syntax. With enough natural language extensions, the parsing engine 204 can derive commands from various ordered linguistic components such as: "Open chart notes for Chuck for his appointment last week . . . Oh, that was Charles Dickens;" or "Can you show the latest open invoices of Jane, please? Last name Austen." For context, the parsing engine 204 can use state from the patient navigation history datastore 206, the patient records datastore 208, the patient profile datastore 210, the provider workflow rules datastore 212, or some other applicable stateful system. The results are provided to the navigation prioritized list datastore 214, which is output to a display device at, e.g., a physician, patient, or other applicable portal.

By making use of context, analytics commands can include "view patients with <Dx>," "view patients taking <drug>," "view patients above <age> without <vaccination>," and "view patients in <geolocation>." Some examples with values for the indicated variables include "view patients with diabetes," "view patients taking opioids," "view patients above 6 months old without seasonal flu vaccine," and "view patients near flash flood warning area in Arizona." Another example of view patients with is "view patients with outstanding invoices."

The command datastore 216 is intended to represent a datastore that includes a command the parsing engine 204 has derived from the input stimuli datastore 202 and context. In some instances, a device, such as a patient monitoring device, may be configured to provide commands in an elemental command syntax, which obviates the parsing engine 204. In other instances, a human, such a physician or agent thereof, can use one or more navigation prioritized lists from the navigation prioritized list datastore 214 to build a command from predicted components and values. In other instances, a human, such as a physician or human or artificial agent thereof, can provide a command in an elemental command syntax without making use of the navigation prioritized lists.

The EHR state update engine 218 is intended to represent an engine that makes changes to an EHR datastore (not shown) in accordance with a command from the command datastore 216. In a specific implementation, some commands do not result in navigation. For example, a human can toggle eRx or electronic prescriptions for controlled substances (EPCS) with an Update command string to toggle on or off In a specific implementation, it is also possible to ask questions to receive helpful answers from an expert system (not shown). Some commands include a navigational component.

The navigation engine 220 is intended to represent an engine that updates the display state datastore 222. In a specific implementation, not all commands trigger the navigation engine 220. Also, incomplete commands may trigger navigation to, e.g., a window at which the command can be completed. For example, if the command is "create appointment for David Thrower," the EHR state update engine 218 may be unable to comply without additional information (e.g., a time and date), so the navigation engine 220 updates the display state datastore 222 to cause an output device to display a page in which the missing data can be provided. Presumably, an output device at a portal displays in accordance with display state. A human, such as a physician or human or artificial agent thereof, can respond to the output device, which may result in an update to the input stimuli datastore 202.

Figure 3:
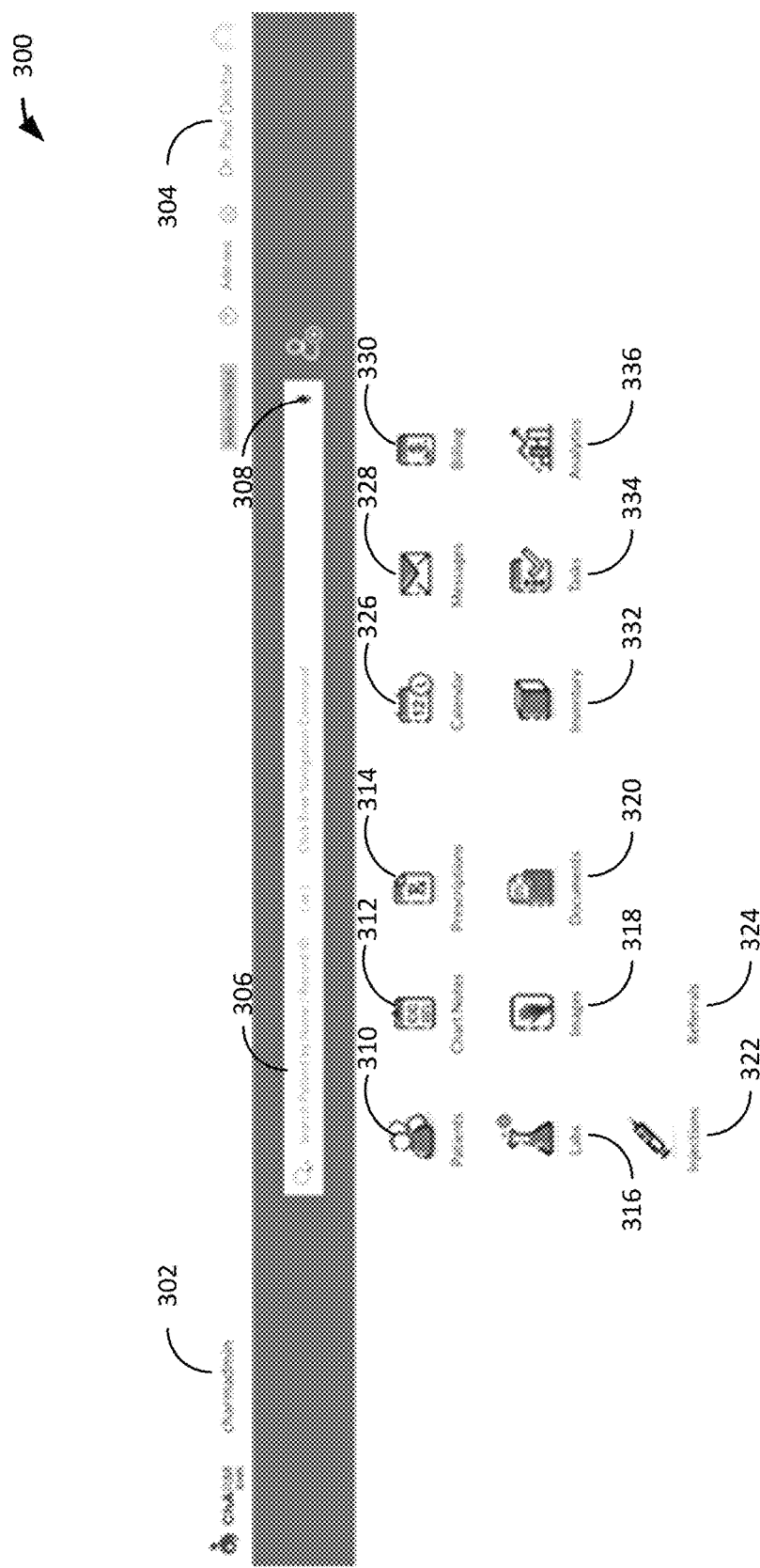
FIG. 3 is a screenshot of an example of an EHR natural language navigation dashboard.

FIG. 3 is a screenshot 300 of an example of an EHR system natural language navigation dashboard. The screenshot 300 includes an administrator name text string 302, a medical service provider name text string 304, a navigation command text box 306, a microphone icon 308, a patients icon 310, a chart notes icon 312, a prescriptions icon 314, a labs icon 316, an images icon 318, a documents icon 320, an injections icon 322, a referrals icon 324, a calendar icon 326, a messages icon 328, a billing icon 330, an inventory icon 332, a tasks icon 334, and an analytics icon 336.

The administrator name text string 302 is an indication of a context of the EHR system natural language navigation dashboard. In a specific implementation, the administrator name text string 302 is an ASCII array, though any applicable text array or image derived therefrom could be used. Context can be used to improve natural language interpretation, predict needs, and maintain a historical log with administrative attribution for activities.

The medical service provider name test string 304 is an indication of a person capable of providing medical services. For illustrative simplicity, it is assumed the medical service provider is the one using the dashboard, though it could be an agent thereof. In a specific implementation, it is desirable to protect EHR-related data, making it essential for applicable systems to require at least username and password to login. In this implementation, the medical service provider name test string 304 can be characterized as a username or a real name or alias associated with a username.

The navigation command text box 306 is an active area into which search terms can be entered, either via text entry, icon selection, voice recognition, or some other suitable technique. Context can be used to interpret input text. For example, a regular expression can be used to match a string of alphanumeric characters to a record identifier or a patient name. Clicking one of the icons 310-324 can populate the navigation command text box 306 with a first part of a command, prompting a human or artificial agent of the system to enter a second part of the command.

In a specific implementation, using context to autosuggest, a list of ordered suggestions is depicted below the navigation command text box 306, from which a human can select a command that has been predicted to be relevant considering the context. The following are examples of parameters that are used to determine the prioritized list of autosuggestions: Knowledge of the patient data in the EHR to show commands that are relevant to the patient (e.g., a cash pay patient would not need to bring up insurance information; a patient with medications to be reviewed every month would benefit from having a medication review and refill; or the like) and the user's workflow (e.g., a physician may have a specific workflow for a patient, such as looking up medical history, looking up a prescription list, entering chart notes, updating prescriptions, providing instructions, and affixing a signature; an insurance biller may have a workflow to look up chart notes and fill out claim forms; or other workflows useful for autosuggesting commands).

The microphone icon 308 is intended to indicate a microphone is provided. In a specific implementation, the microphone icon changes appearance when sounds are detected to let a person viewing the dashboard know the microphone is active. In an implementation that detects sound and converts a subset of the sounds into a command string, a speech recognition engine (not shown) is assumed.

A language syntax suitable for EHR system navigation includes "verbs" with associated actions. Verbs can include, for example, create/new/add (e.g., to create a new record), show/open/view (e.g., to read details of a record), list (e.g., list records matching criteria), edit (e.g., open an edit view to update a record), print (e.g., open a print view), scan (e.g., open a scan view), goto (e.g., go to a specific module or page), and compose (e.g., open a message, note, or other view to compose a new message or note). By typing a verb in the navigation text box 306 or speaking a verb detectable by a language recognition engine associated with the microphone icon 308, a parsing and navigation engine generates a command string with the detected verb.

The command string can be initiated in the navigation text box 306 or via a speech recognition engine. For example, depending upon implementation-specific, configuration-specific, or other factors, the prescriptions icon 314 could be displayed in an active area that, when selected, e.g., with a mouse hover and click, initiates the creation of a Read command string, such as a "list prescriptions" command string. Alternatively, selecting the prescriptions icon 314 initiates the creation of a Create (or Edit) command string, such as "add medication <drug> for <patient>." The "<drug>" variable is intended to represent a variable that can be assigned a value that is uniquely associated with a drug. Typically the drug will be represented in a datastore and identified from typed text or selected from a drop-down menu or the like, but if permitted by the system, the value could be any text, with the understanding some other professional, such as a pharmacist or assistant, would be able to determine a drug unambiguously from the entered or selected value. The "<patient>" variable is intended to represent a variable that can be assigned a value that is uniquely associated with a patient. Alternatively, and as used by way of example in the following few figures, selecting the prescriptions icon 314 initiates the creation of a List command string, such as "prescription for <patient>."

FIG. 4 depicts a screenshot 400 of an example of an EHR system natural language navigation dashboard displaying a command string. The screenshot 400 illustrates a navigation text box 406 displaying a verb (text) string "list." A highlighted selectable drop-down menu item 448 displays a " . . . prescription for <patient>" subject (text) string below the navigation text box 406. The highlighted selectable drop-down menu item 448 can be highlighted as a most-likely choice for a medical professional who is using the EHR system, or an agent thereof, given context. Options other than the highlighted selectable drop-down menu item 448 are subject (text) strings displayed in the selectable drop-down menu items 450-1 to 450-n (collectively, the selectable drop-down menu items 450).

Figure 5:
FIG. 5 depicts a screenshot of an example of an EHR natural language navigation dashboard displaying a completed command string.

FIG. 5 depicts a screenshot 500 of an example of an EHR system natural language navigation dashboard displaying a completed command string. The screenshot 500 illustrates a navigation text box 506 displaying a verb (text) string "list diagnosis for DAVID THROWER." In a specific implementation, as was illustrated in FIG. 4, a subject string option for use with the verb string "list" is " . . . diagnosis for <patient>." The screenshot 500 assumes this option was selected and then a value "DAVID THROWER" for the variable <patient> was typed, spoken, or selected.

Figure 6:
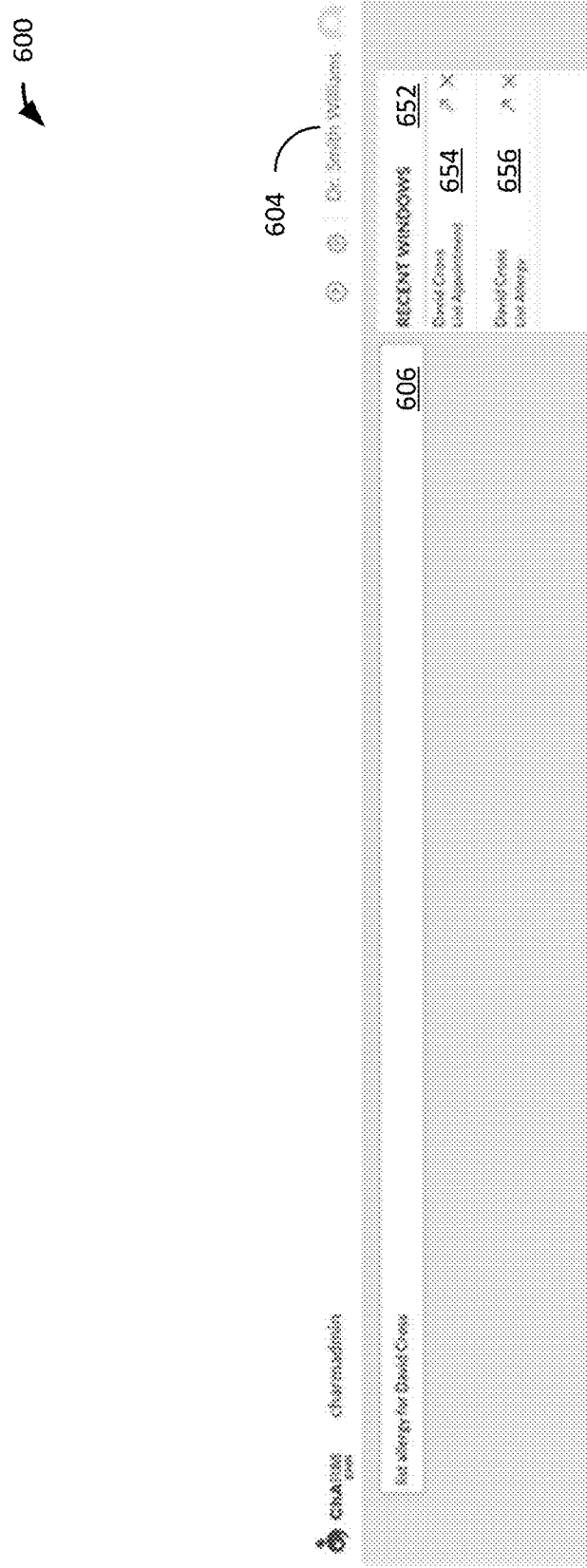
FIG. 6 depicts a screenshot of an example of an EHR natural language navigation dashboard intended to illustrate a use of recent windows.

FIG. 6 depicts a screenshot 600 of an example of an EHR system natural language navigation dashboard intended to illustrate a use of recent windows. A filter can be used to display most recent menu items relevant for a given context, such as by displaying most recent "list" commands after "list" has been identified as the verb of an active command string. A human or artificial agent can record commands, past and present, for easy future access. In the example of FIG. 6, this is accomplished by pinning widgets to a list of Recent Windows, so they are available for easy future access, can be created or destroyed, and live on the familiar desktop-like interface, for frequent use. The screenshot 600 includes a medical service provider name text string 604 that indicates Dr. Smith Williams, or an agent of Dr. Smith Williams, is using the EHR system. The navigation text box 606 displays a command string "list allergy for David Cross." A recent windows box 652 includes a recent entry "David Cross List Appointment" menu item 654 and a "David Cross List Allergy" menu item 656. Windows associated with the menu items 654, 656 can be reopened by clicking on them. It is assumed the menu item 656 was selected to populate the navigation text box 606. The recent windows box 652 can be updated with several menu items that are dependent upon implementation-specific and preference factors.

Generally, when a command string for the verb "list" is initially generated, it is expected a person using the EHR system natural language navigation dashboard wants to view a list of records matching parameters of the command. Table 1 below includes command parameters for a List command not specific to a patient in column 1 and specific to a patient in column 2:

TABLE 1

| Not Patient-Specific | Patient-Specific |
| --- | --- |
| prescriptions | prescription for <patient> |
| images | vaccines for <patient> |
| settings | injections for <patient> |
| resource center | allergies for <patient> |
| patients | lab orders for <patient> |
| chart notes | documents for <patient> |
| labs | charts for <patient> |
| injections | charts to be billed for <patient> |
| calendar | invoices for <patient> |
| messages | stickies for <patient> |
| billing | messages for <patient> |
| inventory | appointments for <patient> |
| tasks | recalls for <patient> |
| analytics | tasks for <patient> |
| | vitals for <patient> |
| | diagnosis < for patient> |
| | quick notes < for patient> |

In a specific implementation, the icons 310-324 shown in FIG. 3 are associated with multiple create verbs for different object types. For example, depending upon implementation-specific, configuration-specific, or other factors, the patients icon 310 could be displayed in an active area that, when selected, e.g., with a mouse hover and click, initiates the creation of a List command string as described above, such as a "list patients" command string. Alternatively, selecting the patients icon 310 initiates the creation of a Create command string, such as "create patient;" the command can open a form including text fields into which patient-specific can be entered either manually or by pulling the relevant data from applicable datastores. Alternatively, selecting the patients icon 310 initiates the creation of a Create command string, such as "create patient<last_name> <first_name> <dob> <gender> <line1> <line2> <city> <state> <zip>" (potentially with punctuation, spacing, or line breaks between the variables).

The table below includes command parameters for a Create command not specific to a patient in column 1 and specific to a patient in column 2:

TABLE 2

| Not Patient-Specific | Patient-Specific |
|---|---|
| patient | prescription for <patient> |
| appointment | vaccine for <patient> |
| invoice | allergy for <patient> |
| inventory | injection for <patient> |
| task | lab orders for <patient> |
| | appointment for <patient> on <mm/dd/yyyy> at <hours:minutes am/pm> with <provider> |
| | chart <type> for <patient> <on mm/dd/yyyy> <with provider> |
| | invoice for <patient> |
| | diagnosis for <patient> |
| | vitals for <patient> |
| | task for <patient> |
| | recall for <patient> |
| | quick notes for <patient> |
| | sticky-note for <patient> |

Alternatively, selecting the patients icon 310 initiates the creation of a Read command string, such as "facesheet for <patient>;" the command can open a window, display, or other display area (referred to as a "facesheet" in this example) in which one or more details of a patient are displayed. An alternative to read that is similar in some respects is a Read command for printing, such as "print facesheet for <patient>." This command would result in a printout being generated for a facesheet specified by a value for the <patient> variable, as described in more detail with reference to FIG. 10 below.

Referring once again to the example of FIG. 3, alternatively, selecting the patients icon 310 initiates the creation of an Update command string, such as "edit facesheet <patient>." Although it may not be desirable to delete a patient for accounting reasons, the ability to delete is one of the four core database functions, which include create, read, update, and delete (CRUD), making a Delete command string such as "delete facesheet <patient>" available in theory if not in practice. However, a patient could be deactivated without removing all patient records from historical datastores with a "deactivate patient <last name> <first name> <dob> <gender> <line1> <line2> <city> <state> <zip>" command (with the variables likely being auto-filled when the last name and first name are entered or replaced with a unique identifier (uid) of the patient).

As another example of a Create command, depending upon implementation-specific, configuration-specific, or other factors, selecting the billing icon 330 initiates the creation of a Create command string, such as "create invoice." Alternatively, selecting the billing icon 330 initiates the creation of a Read command string, such as "invoice <invoice number>;" the command can open a window, display, or other display area (referred to as an "invoice" in this example) in which one or more details of a specific invoice are displayed. An alternative Read command string can be used for printing, such as "print invoice <invoice number>," which would result in a printout being generated for an invoice specified by a value for the <invoice number> variable. Alternatively, selecting the billing icon 330 initiates the creation of an Update command string, such as "edit invoice <invoice number>." Although it may not be desirable to delete an invoice for accounting reasons, a Delete command string such as "delete invoice <invoice number>" is available in theory if not in practice. However, an invoice could be canceled without removing the invoice from historical datastores with a "cancel invoice <invoice number>" command.

The chart notes icon 312 can be selected to CRUD (depending upon implementation-specific, configuration-specific, or other factors) a chart note data structure, or the relevant text can be entered or predictively generated. For example, a Create command string could be "create chart note for <patient>," a Read command string could be "view chart note for <patient>," an Update command string could be "edit chart note for <patient>," and a Delete command string could be "delete chart note for <patient>." An alternative read command string could be "open chart for <patient> on <mm/dd/yyyy> with <provider>."

The labs icon 316 could be selected to CRUD a lab data structure. For example, a Create command string could be "request lab work for <patient>." A Read command string could be "view pending lab results for <patient> <lab result parameter> graph." For example, the "<lab result parameter>" could have a value of hemoglobin such that the Read command string becomes, e.g., "view pending lab results for David Cross hemoglobin graph," which would result in a plotted graph of David Cross' hemoglobin range over the last 6 months.

Some other examples include selecting the calendar icon 326 to generate a Read command string such as "show visits for <date>" or selecting the messages icon 328 to generate a Create command string such as "compose message to <patient/member>." The <date> variable can have a value of today, tomorrow, next <n> days, last <n> days, yesterday, <dd/mm/yyyy> or some other date or range of dates.

Figure 7:
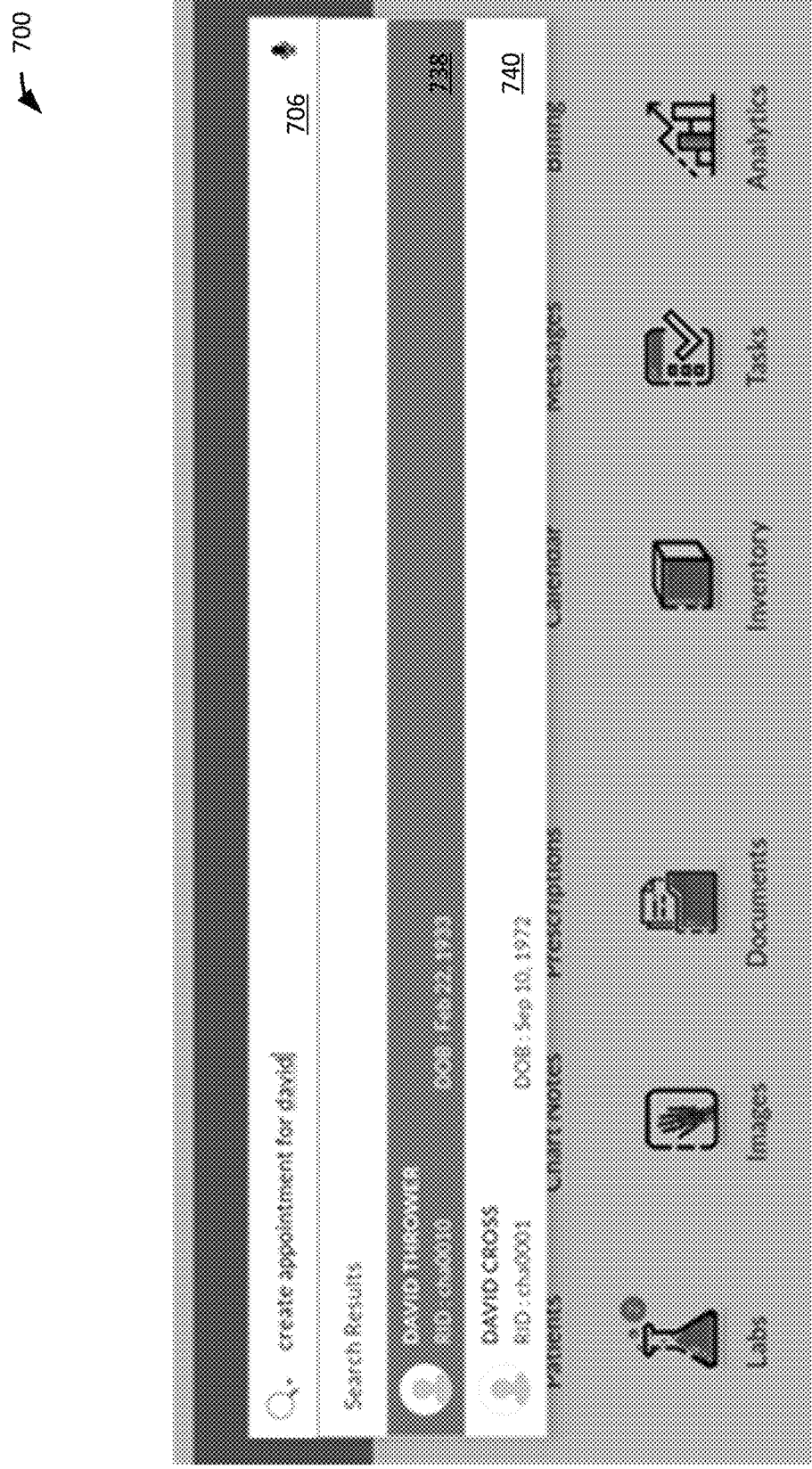
FIG. 7 depicts a screenshot of an example of an EHR natural language navigation dashboard displaying a command string.

FIG. 7 depicts a screenshot 700 of an example of an EHR natural language navigation dashboard displaying a command string. For illustrative purposes, although not shown in the screenshot 700, it is assumed a human entered a "c" via a keyboard and had "create" auto-populate in the navigation text box 706 (not shown) based upon historical choices and context; "appointment for" was then provided as a drop-down menu choice, which the human selected; and the human entered "David" on the keyboard to yield the partial command string "create appointment for David." The drop-down menu item 738 illustrates the human can choose David Thrower and the drop-down menu item 740 illustrates the human can choose David Cross. The drop-down menu items 738 also include a uid ("RID" in this example) and date of birth ("DOB" in this example).

Figure 8:
FIG. 8 depicts a screenshot of an example of an EHR natural language navigation dashboard displaying a command string.

FIG. 8 depicts a screenshot 800 of an example of an EHR natural language navigation dashboard displaying a command string. As is illustrated in the screenshot 700, a human had the option of selecting David Thrower from a drop-down menu, which is assumed to have happened. The navigation text box 806 displays the partial command string "create appointment for David Thrower." The drop-down menu item 842 allows selection of " . . . with <provider>," the drop-down menu item 844 allows selection of " . . . on <mm/dd/yy>," and the drop-down menu item 846 allows selection of " . . . at <hh:mm tt>."

Figure 9:
FIG. 9 depicts a screenshot of an example of an EHR natural language navigation dashboard displaying a command string.

FIG. 9 depicts a screenshot 900 of an example of an EHR natural language navigation dashboard displaying a command string. As is illustrated in the screenshot 800, a human had the option of selecting provider, date, and time for an appointment either by continuing to enter text or by selecting drop-down menu options, which is assumed to have happened. The navigation text box 906 displays the completed command string "create appointment for David Thrower with Dr. Paul Doctor on Jan. 30, 2019 at 5:30 PM."

FIG. 10 is a screenshot 1000 of an example of an EHR natural language navigation dashboard displaying the command string "print facesheet for David Thrower" in a navigation text box 1006. A window 1058 is intended to represent what is displayed upon entering the command, including selectable checkboxes 1060-1 to 1060-*n* (collectively, the selectable checkboxes 1060) and associated descriptions of printable parameters 1062-1 to 1062-*n* (collectively, the descriptions of printable parameters 1062) selected via the selectable checkboxes 1060. By clicking a download button 1064, the printable parameters can be downloaded for display and, if desired, printing.

Figure 11:
FIG. 11 is a screenshot of an example of an EHR natural language navigation dashboard displaying a command string "goto settings" in the navigation text box.

For humans who know precisely where they wish to go, a "goto" command can be useful. FIG. 11 is a screenshot 1100 of an example of an EHR natural language navigation dashboard displaying a command string "goto settings" in the navigation text box 1106. A drop-down menu item 1166 is for " . . . settings," but has not yet faded from view following selection thereof.

Figure 12:
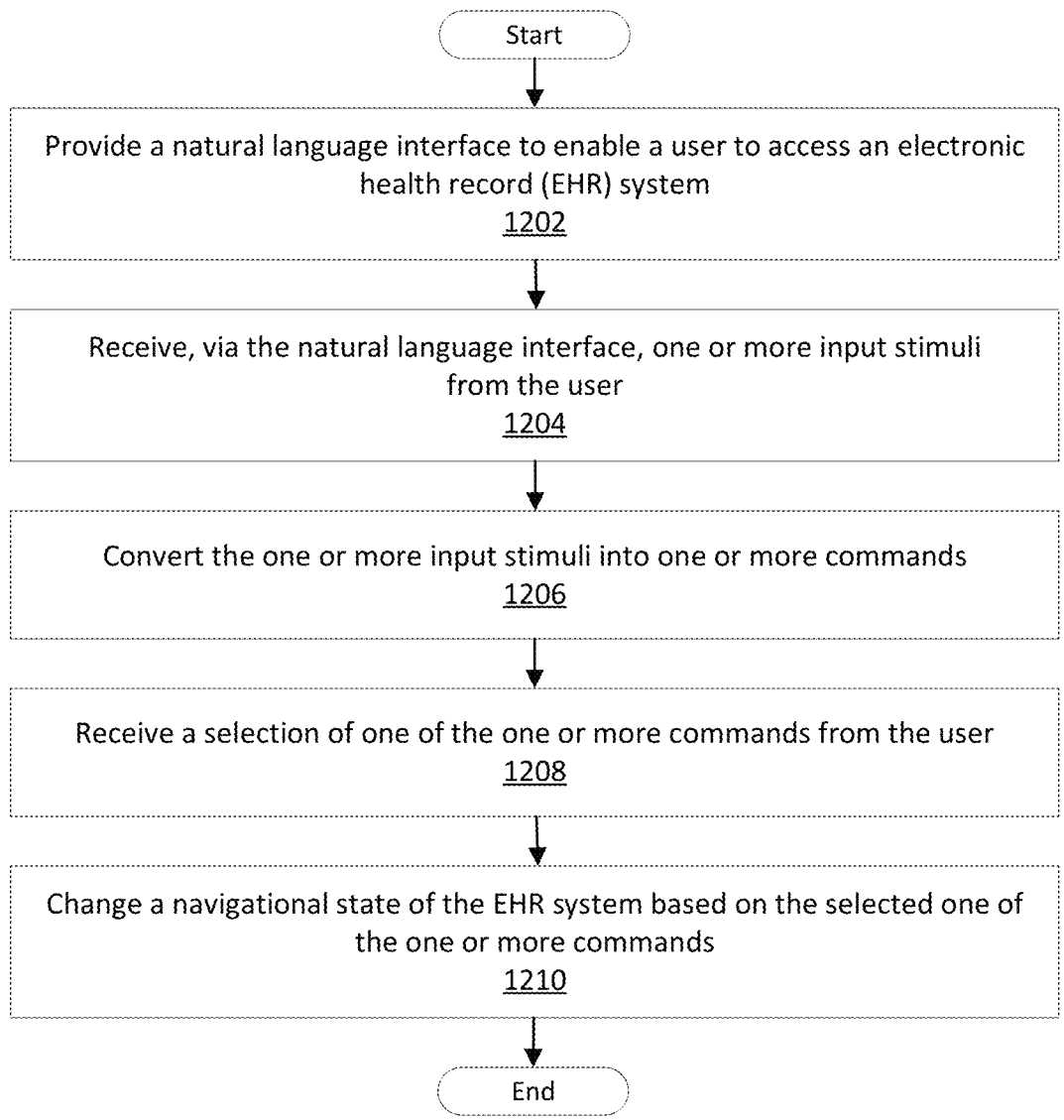
FIG. 12 depicts a flowchart 1200 of an example of a method for enabling a user to efficiently navigate an EHR system.

FIG. 12 depicts a flowchart 1200 of an example of a method for enabling a user to efficiently navigate an EHR system.

The flowchart 1200 begins at module 1202, where a user is provided with a natural language interface to enable the user to access an EHR system. In an embodiment, the natural language interface system is incorporated into an Internet of Things (IoT) device.

The flowchart 1200 continues to module 1204, where one or more input stimuli are received from the user via the natural language interface. In an embodiment, the input stimuli comprises one or more of text, voice, and activation of one or more icons.

The flowchart 1200 continues to module 1206, where the one or more input stimuli are converted into one or more commands. In an embodiment, the one or more input stimuli are converted into the one or more commands using linguistic components stored in a input stimuli datastore. In an embodiment, the one or more commands are displayed in a navigation prioritized list.

The flowchart 1200 continues to module 1208, where a selection of one of the one or more commands is received from the user. In an embodiment, the user selects the one of the one or more commands from a drop-down menu.

The flowchart 1200 continues to module 1210, where a navigational state of the EHR system is changed based on the selected one of the one or more commands as was described previously.

The invention claimed is:

1. A method comprising:
providing a natural language interface to enable a user to access an electronic health record (EHR) system;
receiving, via the natural language interface, one or more first input stimuli from the user, wherein the one or more first input stimuli includes text, sound, and one or more activation of icons, and wherein the sound includes noise, redundancy, and verbosity, each of the noise, the redundancy, and the verbosity including respective data that is not useful for parsing an intended command;
converting the one or more first input stimuli into a plurality of different verbs, each of the verbs associated with a different action performable in the EHR system, wherein the converting includes extracting the noise, the redundancy, and the verbosity from the sound of the input stimuli;
displaying multiple respective command parameters for each of the different verbs, each of the multiple respective command parameters being specific to a patient;
receiving from the user a selection of one of the multiple respective command parameters for each of the different verbs;
receiving, via the natural language interface, one or more second input stimuli from the user, wherein the one or more second stimuli includes second text, second sound, and one or more second activation of icons;
displaying one or more patients having records in the EHR system based on the one or more second input stimuli;
receiving from the user a selection of one of the one or more patients;
converting the plurality of different verbs, the selected multiple respective command parameters, and the selected patient into one or more commands, the one or more commands including the intended command; and
changing a navigational state of the EHR system based on the one or more commands.

2. The method of claim 1, wherein the one or more first input stimuli further comprise voice and activation of one or more icons.

3. The method of claim 1, further comprising displaying the one or more command parameters in a navigation prioritized list.

4. The method of claim 3, wherein a priority of each of the one or more command parameters in the navigation prioritized list is based on a context of the user, a history of past commands, a current workflow, and patient information.

5. The method of claim 1, wherein converting the verb, the selected command parameter, and the selected patient into one or more commands comprises rearranging linguistic components stored in an input stimuli database into a command syntax.

6. The method of claim 1, wherein converting the verb, the selected command parameter, and the selected patient into one or more commands comprises deriving the one or more commands from various ordered linguistic components stored in an input stimuli database.

7. The method of claim 1, wherein converting the verb, the selected command parameter, and the selected patient into one or more commands comprises using one or more navigation prioritized lists to build the one or more commands from one or more of predicted components and predicted values.

8. The method of claim 1, wherein the user is a healthcare provider, a human agent of the healthcare provider, or an artificial agent of the healthcare provider.

9. The method of claim 1, wherein the user is a patient.

10. The method of claim 1, wherein the natural language interface is incorporated into an Internet of Things (IoT) device.

11. An electronic health record (EHR) system comprising:
a natural language interface configured to receive one or more first input stimuli from a user, wherein the one or more first input stimuli includes text, sound, and one or more activation of icons, and wherein the sound includes noise, redundancy, and verbosity, each of the noise, the redundancy, and the verbosity including respective data that is not useful for parsing an intended command;
a display state datastore; and a parsing and navigation engine configured to:
    convert the one or more first input stimuli into plurality of different verbs, each of the verbs associated with a different action performable in the EHR system, wherein the converting includes extracting the noise, the redundancy, and the verbosity from the sound of the input stimuli;
    update the display state datastore to cause an output device to display multiple respective command parameters for each of the different verbs, each of the multiple respective command parameters being specific to a patient;
    receive from the user a selection of one of the multiple respective command parameters for each of the different verbs;
    receive, via the natural language interface, one or more second input stimuli from the user, wherein the one or more second stimuli includes second text, second sound, and one or more second activation of icons;
    update the display state datastore to cause the output device to display one or more patients having records in the EHR system based on the one or more second input stimuli;
    receive from the user a selection of one of the one or more patients;
    convert the plurality of different verbs, the selected multiple respective command parameters, and the selected patient into one or more commands, the one or more commands including the intended command; and
    change a navigational state of the EHR system based on the one or more commands.

12. The system of claim 11, wherein the one or more first input stimuli further comprises voice and activation of one or more icons.

13. The system of claim 11, wherein the natural language interface is configured to display the one or more command parameters in a navigation prioritized list.

14. The system of claim 13, wherein a priority of each of the one or more command parameters in the navigation prioritized list is based on a context of the user, a history of past commands, a current workflow, and patient information.

15. The system of claim 11, wherein converting the verb, the selected command parameter, and the selected patient into one or more commands comprises rearranging linguistic components stored in an input stimuli database into a command syntax.

16. The system of claim 11, wherein converting the verb, the selected command parameter, and the selected patient into one or more commands comprises deriving the one or more commands from various ordered linguistic components stored in an input stimuli database.

17. The system of claim 11, wherein converting the verb, the selected command parameter, and the selected patient into one or more commands comprises using one or more navigation prioritized lists to build the one or more commands from one or more of predicted components and predicted values.

18. The system of claim 11, wherein the user is a healthcare provider, a human agent of the healthcare provider, or an artificial agent of the healthcare provider.

19. The system of claim 11, wherein the user is a patient.

20. The system of claim 11, wherein the natural language interface is incorporated into an Internet of Things (IoT) device.

* * * * *